(12) United States Patent
Kavuturu et al.

(10) Patent No.: US 11,013,453 B2
(45) Date of Patent: May 25, 2021

(54) SURGICAL TOOL WITH PRESSURE SENSOR

(71) Applicant: BOARD OF TRUSTEES OF MICHIGAN STATE UNIVERSITY, East Lansing, MI (US)

(72) Inventors: Srinivas Kavuturu, Okemos, MI (US); Ranjan Mukherjee, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 90 days.

(21) Appl. No.: 16/174,984

(22) Filed: Oct. 30, 2018

(65) Prior Publication Data

US 2019/0125242 A1 May 2, 2019

Related U.S. Application Data

(60) Provisional application No. 62/579,978, filed on Nov. 1, 2017.

(51) Int. Cl.
*A61B 5/00* (2006.01)
*A61B 17/28* (2006.01)
(Continued)

(52) U.S. Cl.
CPC ............ *A61B 5/425* (2013.01); *A61B 5/0053* (2013.01); *A61B 17/282* (2013.01);
(Continued)

(58) Field of Classification Search
CPC ............ A61B 17/2804; A61B 17/2812; A61B 17/2816; A61B 17/282; A61B 17/2841;
(Continued)

(56) References Cited

U.S. PATENT DOCUMENTS 3,136,153 A 6/1964 Kornblau
4,711,240 A * 12/1987 Goldwasser ........... A61B 90/00
606/174
(Continued)

FOREIGN PATENT DOCUMENTS

WO WO-2016/050985 A1 4/2016
WO WO-2017/040680 A1 3/2017

OTHER PUBLICATIONS

Belyaev M.D, O., et al., "Assessment of Pancreatic Hardness—Surgeon versus Durometer," Journal of Surgical Research, vol. 158, No. 1, Jan. 2010, pp. 53-60.
(Continued)

*Primary Examiner* — Katherine H Schwiker
*Assistant Examiner* — Alexis D Amechi
(74) *Attorney, Agent, or Firm* — Harness, Dickey & Pierce, PLC

(57) ABSTRACT

A surgical tool includes opposing jaws, handles and at least one pressure sensor. Another aspect of a surgical tool includes opposing jaws with each having an organ-contacting surface area of at least 50 mm². A further aspect of a surgical tool includes an electronic controller connected to at least one pressure sensor and automatically adapted to calculate or determine an organ-hardness from a sensor when jaws are moved to an organ-compressing position. In yet another aspect of a surgical tool, a pressure sensor is mounted to a pancreas-compressing surface and a displacement transducer or sensor is mounted to and/or located within a handle coupled to the surface, and an electronic controller is mounted to and/or located within the handle for calculating a hardness of a pancreas and/or other organ.

21 Claims, 3 Drawing Sheets

(51) Int. Cl.
*A61B 17/00* (2006.01)
*A61B 90/00* (2016.01)

(52) U.S. Cl.
CPC ...... *A61B 17/2841* (2013.01); *A61B 17/2804* (2013.01); *A61B 2017/00115* (2013.01); *A61B 2017/00818* (2013.01); *A61B 2090/065* (2016.02); *A61B 2505/05* (2013.01); *A61B 2560/0214* (2013.01); *A61B 2562/0247* (2013.01); *A61B 2562/166* (2013.01)

(58) Field of Classification Search
CPC .................. A61B 5/0053; A61B 5/425; A61B 2562/0247; A61B 2562/166; A61B 2090/064; A61B 2090/065
See application file for complete search history.

(56) References Cited

U.S. PATENT DOCUMENTS

| | | | |
|---|---|---|---|
| 5,342,364 A * | 8/1994 | Mikhail | A61B 17/2812 606/79 |
| 5,810,716 A | 9/1998 | Mukherjee et al. | |
| 6,582,451 B1 * | 6/2003 | Marucci | A61B 17/29 606/207 |
| 6,770,081 B1 | 8/2004 | Cooper et al. | |
| 6,852,107 B2 | 2/2005 | Wang et al. | |
| 7,413,565 B2 | 8/2008 | Wang et al. | |
| 8,527,094 B2 | 9/2013 | Kumar et al. | |
| 8,756,711 B2 | 6/2014 | Plodinec et al. | |
| 9,259,232 B2 | 2/2016 | Esanu | |
| 2005/0165429 A1 * | 7/2005 | Douglas | A61B 17/08 606/157 |
| 2007/0049920 A1 | 3/2007 | McClurken et al. | |
| 2010/0200636 A1 * | 8/2010 | Zemlok | A61B 17/068 227/175.1 |
| 2012/0271555 A1 | 10/2012 | Levental et al. | |
| 2014/0039512 A1 * | 2/2014 | He | A61B 17/295 606/110 |
| 2015/0224326 A1 | 8/2015 | Toth et al. | |
| 2015/0297284 A1 | 10/2015 | McClurken et al. | |
| 2016/0135745 A1 * | 5/2016 | Chang | A61B 5/6806 600/301 |
| 2016/0338760 A1 * | 11/2016 | Houser | A61B 90/08 |
| 2017/0095205 A1 | 4/2017 | Abreu | |
| 2017/0172550 A1 * | 6/2017 | Mukherjee | A61B 5/022 |
| 2017/0296178 A1 * | 10/2017 | Miller | A61B 5/0261 |

OTHER PUBLICATIONS

Kavuturu, S. et al., "Lymphoepithelial Cysts of the Pancreas. Can Preoperative Imaging Distinguish This Benign Lesion from Malignant Cystic Pancreatic Lesions?" Journal of the Pancreas, vol. 14, No. 3, May 10, 2013, pp. 250-255.

Moromugi, S. et al., "A Sensor to measure hardness of human tissue," IEEE Sensors, Oct. 22-25, 2006, 4 pages.

Darvish, B. et al., "A Novel Tactile Force Probe for Tissue Stiffness Classification," American Journal of Applied Sciences 6 (3), 2009, pp. 512-517.

Hong, T. et al., "Pancreatic Hardness: Correlation of surgeon's palpation, durometer measurement and preoperative magnetic resonance imaging features," World Journal of Gastroenterology 23 (11), Mar. 21, 2017, pp. 2044-2051.

Lee, J. et al., "A Micro-Fabricated Force Sensor Using an All Thin Film Piezoelectric Active Sensor," www.mdpi.com/journal/sensers, 2014, pp. 22199-22207.

"What is a Linear Variable Displacement Transducer?" www.omega.com/technical-learning/linear-variable-displacement-transducers.html, Oct. 13, 2017, 3 pages.

Schaevitz, L., "Finding the right sensor for linear displacement," www.machinedesign.com, Oct. 13, 2017, 9 pages.

"3046 Linear Motion Potentiometer," Bournes, 2015, 1 page.

"Model KS Sanitary Transmitter," Ashcroft, Bulletin PT-6, 2014, 2 pages.

"Pressure Transducer Capabilities," Ashcroft, Bulletin TC-1, 2013, 4 pages.

"Bourns 3046L-3-103," Mouser Electronics, 2017, 1 page.

"Teensy-LC Without Pins," Product ID 2419, www.adafruit.com/product/2419, Oct. 2017, 6 pages.

"FSR Force Sensing Resistor Integration Guide and Evaluation Parts Catalog," Interlink Electronics, published prior to Nov. 2017, 26 pages.

"Shore Durometer HPSO," Schmidt Control Instruments, www.hans-schmidt.com, Oct. 2017, 6 pages.

"Force Sensor Resistor—Square," Karlsson Robotics, www.kr4.us, Oct. 2017, 5 pages.

* cited by examiner

SURGICAL TOOL WITH PRESSURE SENSOR

CROSS-REFERENCE TO RELATED APPLICATIONS

This application claims the benefit of U.S. Provisional Application No. 62/579,978, filed on Nov. 1, 2017. The entire disclosure of the above application is incorporated by reference herein.

BACKGROUND AND SUMMARY

The present disclosure generally relates to surgical tools and more particularly to a surgical tool with a pressure sensor.

It is known that a soft pancreas and small pancreatic duct can lead to post-operative pancreatic leaks and fistulas. However, there is no currently available tool for use in objectively determining softness or hardness of the pancreatic tissue and, by default, it is traditionally determined in a subjective manner by the operating surgeon. This approach lacks accuracy and is difficult to perform with less experienced surgeons.

Crude experimental attempts to objectively measure pancreatic hardness are disclosed within the following publications: (a) T. Hong, et al., *Pancreatic Hardness: Correlation of Surgeon's Palpation, Durometer Measurement and Preoperative Magnetic Resonance Imaging Features,* World J. Gastroenterology, vol. 23, issue 11, p. 2044 (Mar. 20, 2017); and (b) O. Belyaev, et al., *"Assessment of Pancreatic Hardness—Surgeon Versus Durometer,"* J. Surgical Research, vol. 158, no. 1, p. 53 (January 2010). While these publications recognize the surgical need for objective measurements, the conventional durometer gauges employed disadvantageously only provided localized point-contact and did not automatically calculate pancreas-specific results.

Furthermore, a medical tool flowing fluid to a tissue while heating the tissue is disclosed in U.S. Patent Publication No. 2007/0049920 entitled "Fluid-Assisted Medical Devices, Fluid Delivery Systems and Controllers for Such Devices, and Methods" which published to McClurken et al. on Mar. 1, 2007, and is incorporated by reference herein. This tool employs jaws having multiple electrodes, however, this conventional electrosurgical tool is intended for use in coagulation and/or cutting of tissue.

In accordance with the present invention, a surgical tool includes opposing jaws, handles and at least one pressure sensor. Another aspect of a surgical tool includes opposing jaws with each having an organ-contacting surface area of at least 50 mm². A further aspect of a surgical tool includes an electronic controller connected to at least one pressure sensor and automatically adapted to calculate or determine an organ-hardness from a sensor when jaws are moved to an organ-compressing position. In yet another aspect of a surgical tool, a pressure sensor is mounted to a pancreas-compressing surface and a displacement transducer or sensor is mounted to and/or located within a handle coupled to the surface, and an electronic controller is mounted to and/or located within the handle for calculating a hardness of a pancreas and/or other organ. Methods of manufacturing and/or using any of the preceding surgical tool aspects are also provided.

The present surgical tool is advantageous over traditional approaches. For example, the present surgical tool is expected to provide repeatable and objective pancreas hardness results during surgical and/or laboratory test situations. Furthermore, the present surgical tool can be sterilized without harm for surgical re-use in one embodiment or inexpensively manufactured for a single use in another embodiment. Additionally, the present surgical tool is advantageous by providing a large surface area on the opposing jaws to simultaneously compress a wide area of the pancreas and/or other organ therebetween, as contrasted to the undesirable point-loading of some conventional durometer gauge experiments. The electronic control and programmed software instructions of the present surgical tool allow for automated and quick calculations and/or determinations of pancreatic and other organ hardness in essentially a real-time manner during a surgical procedure; this advantageously shortens the duration of the surgery and are expected to provide more accurate results which are not dependent upon surgeon-to-surgeon variability. Additional features and benefits of the present surgical tool will become apparent from the following description and appended claims, taken in conjunction with the accompanying drawings.

DETAILED DESCRIPTION

Figure 1:
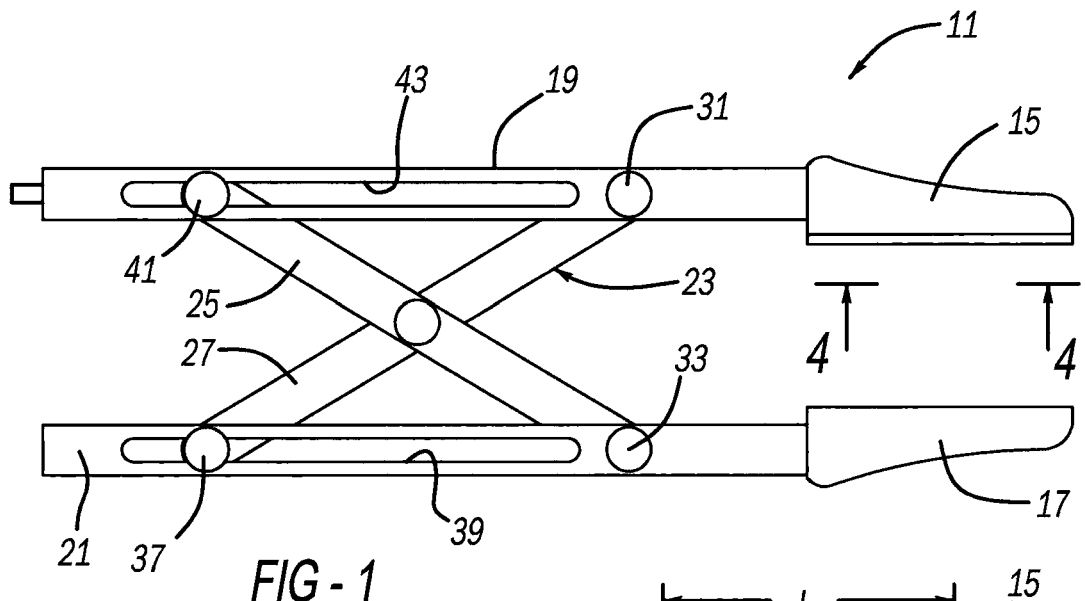
FIG. 1 is a side elevational view showing the present surgical tool in an open position.

Referring to FIGS. 1-4, a preferred embodiment of a surgical tool 11 is used for determining the hardness or stiffness of an organ, such as a pancreas 13, of a human patient. Tool 11 has a clamp-like configuration including a pair of opposed jaws 15 and 17 coupled to handles 19 and 21, respectively. Handles 19 and 21 include hollow internal segments which are open facing toward each other, such that these segments have a generally U-shape.

A linkage assembly 23 includes a pair of scissor links 25 and 27 which moveably couple together handles 19 and 21. A pivot pin 31 couples a forward end of link 27 to a hole through sidewalls of handle 19 with a stationary pivot axis. Similarly, a pivot pin 33 couples a forward end of link 5 to a hole through sidewalls of handle 21 with a stationary pivot axis. A central pivot pin 35 couples together central sections of links 25 and 27 in a crossing or scissor linkage arrangement. Another pivot pin 37 moveably couples a trailing end of link 27 within a fore-and-aft elongated slot 39 through at least one sidewall of handle 21. Similarly, a pivot pin 41 moveably couples a trailing end of link 25 within a fore-and-aft elongated slot 43 of handle 19.

A compression spring 51 is located within a hollow end segment of handle 21 and secured thereto by a shoulder bolt fastener 53, integrally molded pin, or the like. A forward facing end of fastener 53 also serves as a mechanical stop abutting the slideable trailing end of link 27. A coupler 55 couples pivot pin 37 or alternately, the trailing end of link 27, to a forward end of spring 51. Thus, spring 51 linearly biases and pushes trailing end of link 27 in a forward direction, which in turn, urges linkage assembly 23 and jaws 15 and 17 toward their open position shown in FIGS. 1 and 3. Alternately, spring 51 can be oriented perpendicular to the fore-and-aft orientation of handle 21, with its free end operably directly compressing against handle 19.

A linear variable displacement transducer or sensor 61 is located within the hollow segment of handle 19. This displacement sensor is an electromechanical device which converts mechanical motion into a variable electrical current, voltage or electric signals. An armature or plunger 63 extending from sensor 61 is coupled to pivot pin 41 or the trailing end of link 25 to detect and measure forward and rearward linear movement thereof when jaws 15 and 17 are moved toward and away from each other. An exemplary potentiometer type of linear sensor 61 is model 3046 from Bourns, Inc.

A printed circuit board 71 includes an electrical circuit with electronic components such as a microprocessor controller 73, RAM or ROM memory 75, a Bluetooth, wi-fi or other wireless transmitter 77, and a rechargeable battery 79 mounted on printed circuit board 71. Printed circuit board 71 and the associated electronics are sealed inside a hollow housing segment of handle 19 which is enclosed by a sealed lid 81. A wire 83 or stamped metal lead connects sensor 61 to the electrical circuit on printed circuit board 71. Furthermore, electrical connectors 85 project from or are recessed within an end of handle 19 or are otherwise accessible to mate with a removeable battery charger 87, connected to a power supply 89. Data may also be downloaded via the charger. Moreover, transmitter 77 optionally sends output signals to a remote computer 91 which contains a microprocessor, an input device such as a keyboard 93, and output devices such as a display screen 95 and a printer. An exemplary PCB 71 and electrical circuit is Teensy—LC product No. 2419. Alternately, a small display screen or other indicator may be externally mounted directly on handle 19 to display output text, numbers or graphic images as dictated by controller 73.

A thin film pressure transducer 101 is attached to jaw 15. Pressure transducer 101 may be of the type disclosed in J. Lee, et al., "*A Micro-Fabricated Force Sensor Using an All Thin Film Piezoelectric Active Sensor*," Sensors 14, ISSN 1424-820, p. 22199 (Nov. 25, 2014). Force sensor is electrically connected to the printed circuit board 71 via an electric wire 103, metal trace, or the like located within a recessed groove in an outer wall of handle 19. A latex film coating 105 or the like is located on the pancreas contacting surface 107 of pressure sensor 101. Exemplary pressure transducers 101 are Force Sensing Resistor polymer thick film from Interlink Electronics Inc. and a force sensitive resistor part no. SEN-09376 from Karlsson Robotics Inc.

Alternately, different pressure sensors may be employed such as a polysilicon CVD thin film sensor, a MEMS silicone capacitive sensor, a MEMS isolated piezoelectric sensor, or the like. Moreover, it is alternately envisioned that multiples of pressure sensor 101 can be placed on both jaws 15 and 17, or less preferably on the linkage assembly. It is also envisioned that the printed circuit board and sensors may be alternately mounted on the same handle with spring 51. And, the sliding pivot pins may instead be on the forward ends of the links rather than on the illustrated trailing ends.

The handles and jaws of tool 11 are made of stainless steel if they are to be sterilized and reused. But, it is also envisioned that the handles and jaws can be injection molded or additively layered by three-dimensional printing, or the like, if they are to be discarded after a single use. If the discarded and less expensive embodiment is used, then the printed circuit board may be entirely or partially located on the remote charger 87 or incorporated into the remote computer 91 to further reduce expense.

Figure 4:
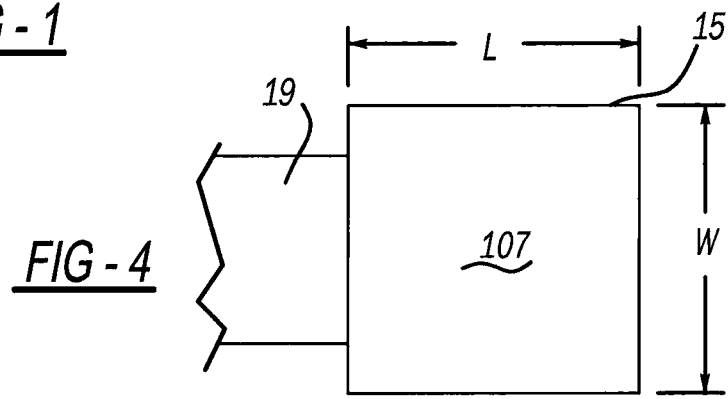
FIG. 4 is a fragmentary elevational view, in the direction of arrow 4-4 from FIG. 1, of the present surgical tool.
Figure 2:
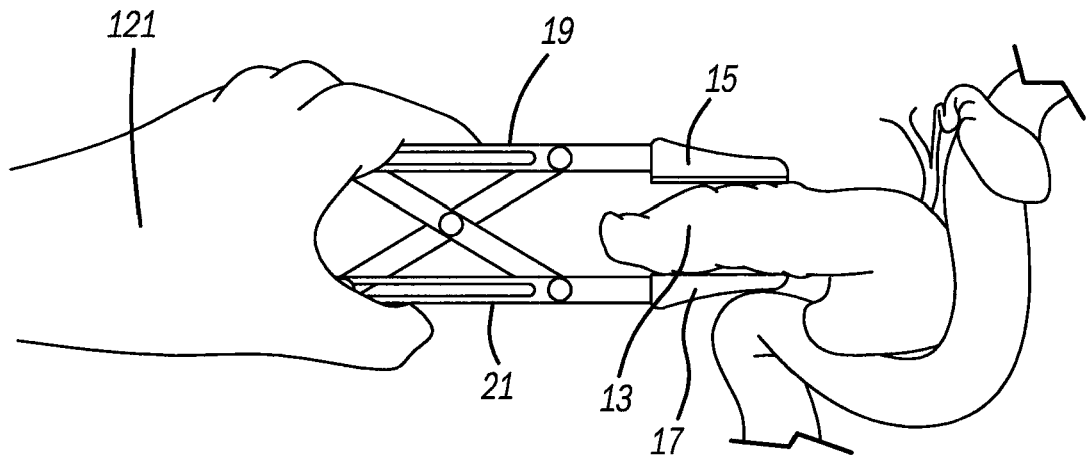
FIG. 2 is a side elevational view showing the present surgical tool in a pancreas-compressing position.

As shown in FIG. 4, the length L and width W are preferably of rectangular shape and even more preferably of equal dimensions, to provide a large and simultaneous contact area to compress the pancreas in a non-point loading fashion. For example, the surface area of contacting surface 107 of both jaws 15 and 17 are preferably at least 50 mm$^2$ and more preferably at least 100 mm$^2$ and even more preferably approximately 645 mm$^2$ (1 inch$^2$). In surgical use, it is advantageous to compress the pancreas in multiple different locations to obtain an average hardness measurement. However, this approach is expected to be much more accurate and much faster than localized point compression with traditional simple durometer gauges.

When the surgeon 121 compresses the two handles 19 and 21 toward each other manually with his or her hand, the trailing pivot pins 37 and 41 will linearly slide rearward within slots 39 and 43, respectively. This will cause jaws 15 and 17 to linearly move toward each other their facing contacting surfaces 107 will remain essentially parallel to each other. The jaws will thereby compress the pancreas while still providing tactile feel to the surgeon who can prevent overcompensation. When the surgeon releases pressure on the handles, spring 53 will cause the jaws to retract away from each other to release the pancreas.

Figure 3:
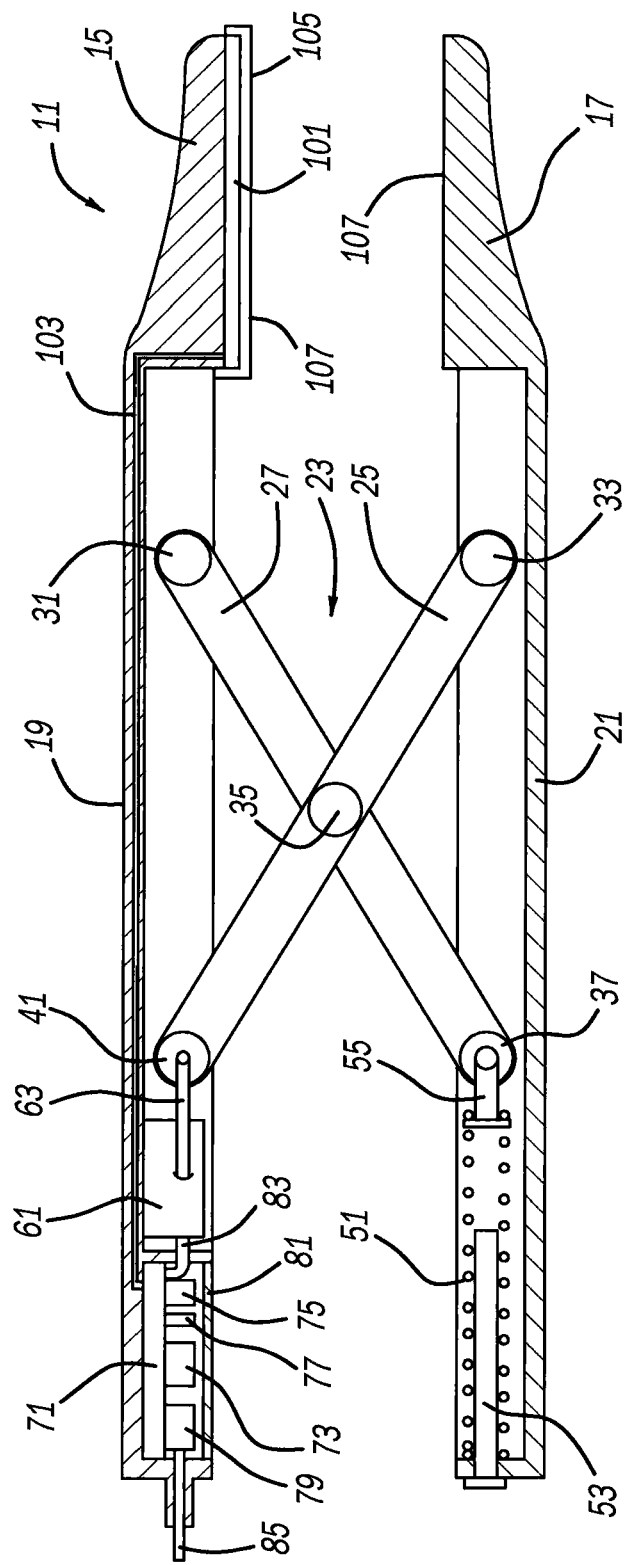
FIG. 3 is a partially cross-sectional and partially perspective view of the present surgical tool.
Figure 3:
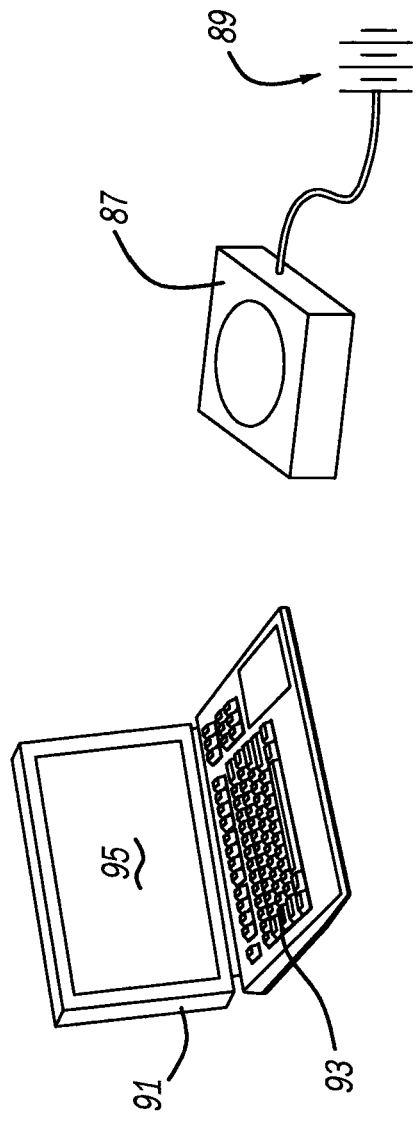
Figure 5:
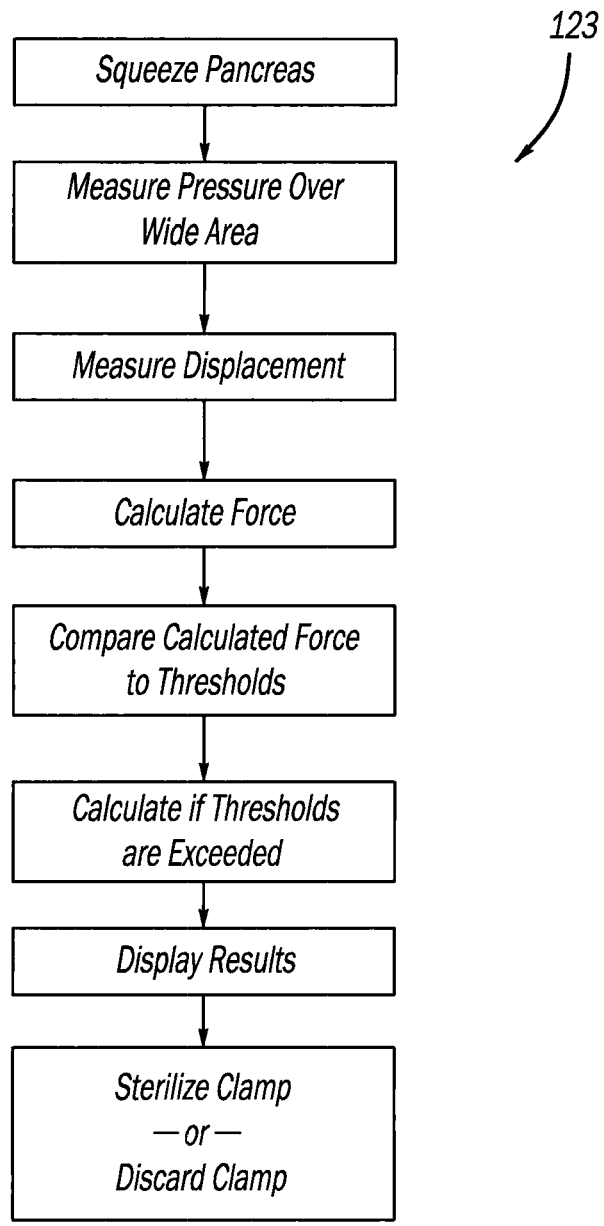
FIG. 5 is a flow diagram showing software logic of a controller employed with the present surgical tool.

Programmed software instructions 123, stored in memory 75 and operated within controller 73, act as follows with reference to FIGS. 3 and 5. Pressure sensor 101 will measure the jaw pressure against the pancreas over a wide area. Substantially simultaneously, displacement sensor 61 will sense and measure the displacement of jaws 15 and 17 indirectly through linkage assembly 23. Signals will be sent from the sensors to controller 73 which will then calculate or determine the force. The controller then compares the calculated force to previously input or predetermined thresholds. These thresholds are obtained by conducting tests with the present tool on healthy and unhealthy pancreases of test subjects and/or prior patients. Thereafter, controller 73 calculates or determines if the thresholds are exceeded and displays the results on computer 91 or the tool-mounted display.

It is alternately envisioned that the present surgical tool 11 can be modified to be actuated through an endoscope or with a minimally invasive robotic surgical machine. Examples of such endoscopes and robots are disclosed in U.S. Pat. No. 9,259,232 entitled "Surgical Endoscope Device With Detachable End Tool as a Clamp" which issued to Esanu on Feb. 16, 2016, and U.S. Pat. No. 6,770,081 entitled "In Vivo Accessories for Minimally Invasive Robotic Surgery and Methods" which issued to Cooper et al. on Aug. 3, 2004. Both of these patents are incorporated by reference herein.

While various embodiments of the present surgical tool have been disclosed herein, it is also envisioned that other variations may be made. For example, a cam-and-cam follower may be employed as part of or instead of linkage assembly 23. Furthermore, other linkage shapes, quantities and mechanisms may alternately be used, although some of the present advantages may not be fully realized. For example, a pliers-type construction of pivoting handles and/or jaws may be employed with some sensor aspects but rotational jaw movement is much less desired than parallel jaw movement. A Peaucellier linkage may alternately be employed if the tool is of larger size. Moreover, the handles may be provided with different shapes and geometries, however, some of the present advantages may not be achieved. It is intended by the following claims to cover these and any other departures from the disclosed embodiments which fall within the true spirit of this invention.

The invention claimed is:

1. A surgical tool comprising:
opposing jaws each having a flat organ-contacting surface area of at least 50 mm$^2$;
two handles coupled to the jaws, movement of the two handles causing the jaws to selectively move toward and away from each other such that the flat organ-contacting surfaces of the jaws move substantially parallel to each other between a fully open position and an organ-compressing position;
at least one pressure sensor coupled to at least one of the jaws; and
an electronic controller connected to the at least one pressure sensor and being adapted to automatically calculate an organ-hardness when the jaws are moved to the organ-compressing position;
linkages coupled together by a main pivot;
the two handles moveably coupled together by the linkages;
the two handles including hand-gripping surfaces such that when a surgeon moves the two handles toward each other, the jaws move toward the organ-compressing position;
the two handles being elongated along substantially parallel centerlines; and
the flat organ-contacting surface areas of the jaws being substantially parallel to the elongated centerlines of the two handles at all times.

2. The surgical tool of claim 1, wherein:
the linkages and main pivot define a scissor linkage mechanism with a first end of each of the linkages being rotatably mounted to an associated one of the two handles by a fixed pivot, and an opposite second end of each of the linkages being slideably and rotatably mounted to an associated one of the two handles by a traversing pivot; and
each of the jaws including a tapered outer surface opposite the flat organ-contacting surface area such that each of the jaws has a substantially triangular side view shape.

3. The surgical tool of claim 1, further comprising:
a displacement sensor sensing a travel distance associated with movement of the jaws, the displacement sensor sending an electrical signal to the electronic controller which the electronic controller uses in an automatic calculation; and
at least one of the displacement sensor and the electronic controller, being located within a hollow area of at least one of the two handles.

4. The surgical tool of claim 3, wherein the displacement sensor is attached to one of the two handles and the at least one pressure sensor is on an organ-compressing side of the associated jaw.

5. The surgical tool of claim 1, wherein:
the electronic controller is configured to determine the organ-hardness of a pancreas during surgery in substantially real-time; and
at least one of the jaws directly extends in a straight line from an elongated centerline of at least one of the two handles with the flat organ-contacting surface area being parallel to the elongated centerline.

6. The surgical tool of claim 1, further comprising:
a pancreas organ-contacting film coating;
the at least one pressure sensor being a film pressure transducer affixed to the associated jaw on the entire flat organ-contacting surface area, the pancreas organ-contacting film coating covering the at least one pressure sensor;
a printed circuit board mounted to one of the two handles; and
an electrical conductor connecting the film pressure transducer to the printed circuit board.

7. The surgical tool of claim 6, wherein the electronic controller is affixed to the printed circuit board, further comprising a spring biasing the jaws toward the fully open position.

8. The surgical tool of claim 1, further comprising:
a rechargeable battery mounted to one of the two handles;
a display screen remotely located away from the jaws and the two handles;
the electronic controller being mounted to one of the two handles; and
the organ hardness being displayed on the remotely located display screen.

9. The surgical tool of claim 1, further comprising:
a displacement sensor sensing movement of at least one of the linkages relative to an associated one of the two handles.

10. A surgical tool comprising:
opposing jaws each having an organ-contacting surface;
handles coupled to the jaws, movement of the handles causing the jaws to move toward and away from each other;
a pressure sensor operably sensing organ-compressing jaw pressure without point-loading;
a displacement sensor operably sensing a movement distance change associated with closure of the jaws; and
an electronic controller connected to the pressure sensor and the displacement sensor, the electronic controller being adapted to calculate an organ-hardness when the jaws are moved to an organ-compressing position;
a display screen indicating the calculated organ hardness;
the electronic controller being configured to determine the organ-hardness during surgery in substantially real-time; and
at least one of the jaws directly extending in a straight line from an elongated centerline of an associated one of the handles with a flat organ-contacting surface area being parallel to the elongated centerline.

11. The surgical tool of claim 10, further comprising:
a linkage mechanism coupling together the handles;
a spring biasing the handles away from each other; and
the handles are adapted to fit within a single hand of a user when an organ is compressed by the jaws.

12. The surgical tool of claim 10, wherein:
the electronic controller is mounted to one of the handles;
the pressure sensor is affixed to the organ-contacting surface of one of the jaws; and
the displacement sensor is a linear variable transducer mounted to one of the handles.

13. The surgical tool of claim 10, wherein the jaws are configured to compress the organ, which is a pancreas, during surgery, and the organ-hardness is pancreas hardness.

14. A surgical tool comprising:
opposing jaws each having an organ-contacting surface;
handles coupled to the jaws, movement of the handles causing the jaws to move toward and away from each other;
a pressure sensor operably sensing organ-compressing jaw pressure without point-loading;

a displacement sensor operably sensing a movement distance change associated with closure of the jaws; and an electronic controller connected to the pressure sensor and the displacement sensor, the electronic controller being adapted to calculate an organ-hardness when the jaws are moved to an organ-compressing position;

a display screen indicating the calculated organ hardness;

a linkage mechanism coupling together the handles;

a spring biasing the handles away from each other; and the handles are adapted to fit within a single hand of a user when an organ is compressed by the jaws;

wherein the linkage mechanism includes crossing scissor linkages rotatably coupled at a main pivot and having handle pivots rotatably coupled to the handles.

15. The surgical tool of claim 14, wherein the jaws linearly project from ends of the handles such that the organ-contacting surfaces of the jaws move substantially parallel to each other between a fully open position and the organ-compressing position.

16. The surgical tool of claim 14, wherein:

the electronic controller determines pancreas-hardness during surgery in substantially real-time; and at least one of the jaws directly extends in a straight line from an elongated centerline of the at least one handle of the handles with a flat organ-contacting surface area being parallel to the elongated centerline.

17. The surgical tool of claim 14, wherein the jaws are configured to compress the organ, which is a pancreas, during surgery, and the organ-hardness is pancreas hardness.

18. A surgical tool comprising:

opposing pancreas-contacting surfaces;

handles coupled to the pancreas-contacting surfaces and the handles being graspable within a single hand of a surgeon;

a pancreas-pressure sensor mounted to a first of the pancreas-contacting surfaces, the pancreas-pressure sensor including a polymeric film and a resister;

a displacement sensor operably sensing a movement change associated with the pancreas-contacting surfaces;

an electronic controller mounted on one of the handles receiving signals from the pancreas-pressure and displacement sensors;

an output indicating a pancreas-hardness value calculated by the electronic controller; and the pancreas-contacting surfaces being substantially parallel when compressing the pancreas.

19. The surgical tool of claim 18, further comprising:

linkages coupling together the handles;

a spring biasing the handles away from each other;

a display screen showing the output indicating the pancreas-hardness value calculated by the electronic controller;

the handles being adapted to fit within a single hand of a user when an organ is compressed by the jaws;

at least one of the sensors or the electronic controller, being located within a hollow area of the handles; and each of the pancreas-contacting surfaces have an area of at least 50 mm$^2$.

20. The surgical tool of claim 18, further comprising a scissor linkage mechanism including multiple linkages and a main pivot, with a first end of each of the linkages being rotatably mounted to an associated one of the handles by a fixed pivot, and an opposite second end of each of the linkages being slideably and rotatably mounted to an associated one of the handles by a traversing pivot.

21. The surgical tool of claim 18, wherein each of the jaws includes a tapered outer surface opposite the pancreas-contacting surface, which is substantially flat, such that each of the jaws has a substantially triangular side view shape.

* * * * *